United States Patent [19]

Brown

[11] 4,073,590
[45] Feb. 14, 1978

[54] LASER TOTAL REFLECTOMETER
[75] Inventor: R. Bernard Brown, Upper Marlboro, Md.
[73] Assignee: The United States of America as represented by the Secretary of the Navy, Washington, D.C.
[21] Appl. No.: 742,815
[22] Filed: Nov. 18, 1976
[51] Int. Cl.² .................................................. G01N 21/48
[52] U.S. Cl. ........................................ 356/209; 356/210
[58] Field of Search .................. 356/209, 210, 211, 212

[56] References Cited
U.S. PATENT DOCUMENTS
2,311,101  2/1943  Tuttle ..................................... 356/210

Primary Examiner—Vincent P. McGraw
Assistant Examiner—Rodney B. Bovernick
Attorney, Agent, or Firm—R. S. Sciascia; Philip Schneider; Melvin L. Crane

[57] ABSTRACT

A device for measuring the total reflectivity, i.e., specular plus scatter, of a small area of a material at various laser frequencies and intensities. The device includes appropriate transmitting and collecting optics in conjunction with a thermopile-type energy sensor with an external metering circuit. The metering circuit can be quickly adjusted to read total reflectivity of a sample placed in front of the reflectivity-measuring device.

7 Claims, 2 Drawing Figures

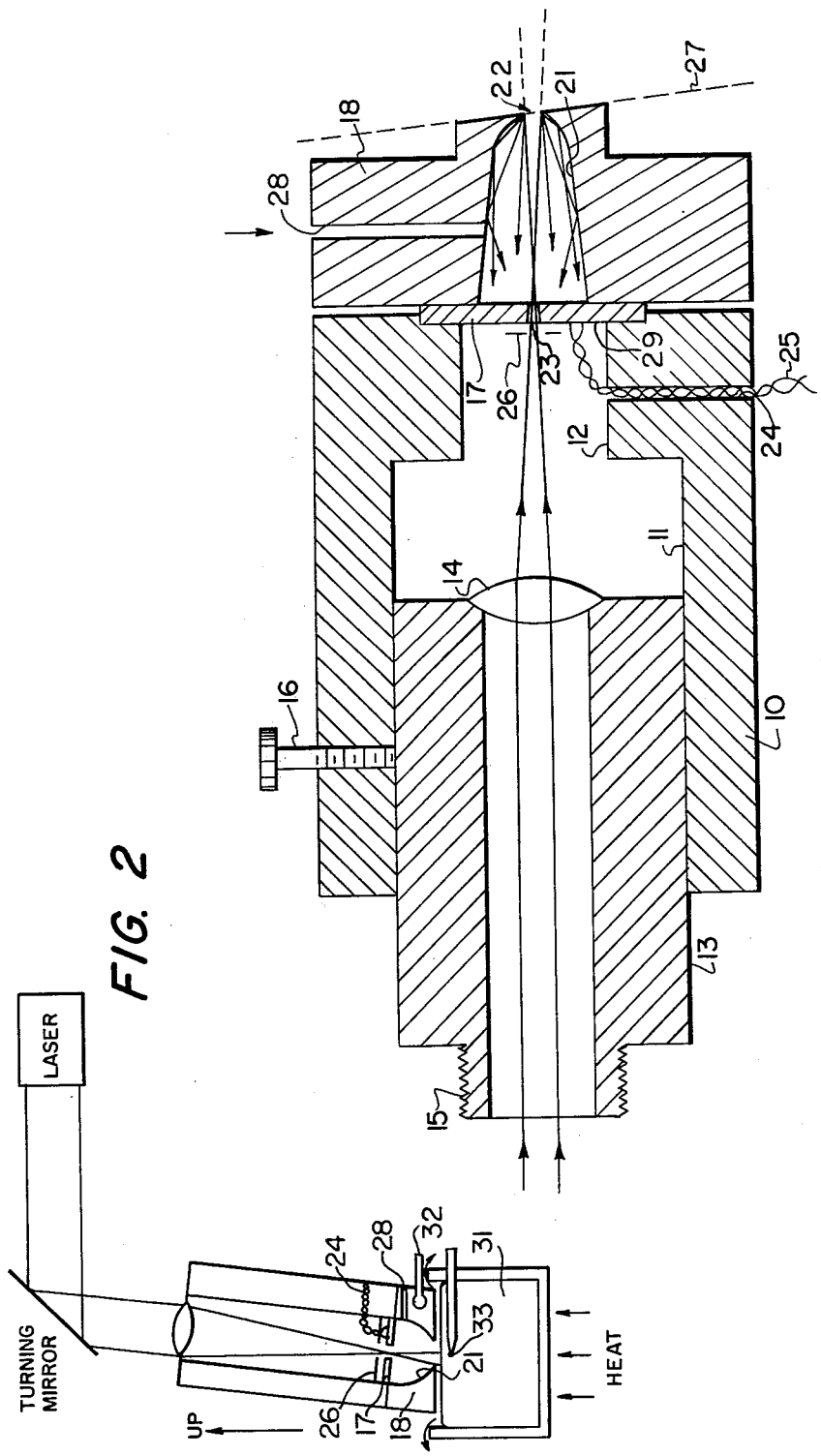

LASER TOTAL REFLECTOMETER

BACKGROUND OF THE INVENTION

The invention is directed to a device for measuring total reflectivity, i.e., specular plus scatter, of various surfaces at various laser frequencies and intensities.

Heretofore various equipments have been used to measure the diffuse reflection density of a surface. One such instrument, shown in U.S. Pat. No. 2,311,101, measures light reflected at a certain large angle greater than 10° from a diffuse surface illuminated normal to the surface. A converging beam is focused onto the suface and some of the light is reflected back and detected by a photoelectric cell.

SUMMARY OF THE INVENTION

This device measures total reflectivity, i.e., specular and scatter, of various laser frequencies and intensities by focusing laser radiation through a small passage in a thermopile sensor, a passage through a mirrored surface, and through a small opening in the mirrored passage onto the test surface. Reflected radiation is detected by the sensor and an output therefrom is measured to denote the reflectivity of the surface. The device is simple in structure, accurate, easy to operate, and it measures total reflection even for molten materials.

BRIEF DESCRIPTION OF THE DRAWING

FIG. 1 is a cross-sectional view illustrating the various parts.

FIG. 2 illustrates a device for measuring molten material.

DETAILED DESCRIPTION

The device includes a cylindrical body 10 having a coaxial passage 11 of large diameter extending along the body from one end to a smaller-diameter passage 12 of shorter length which extends to the opposite ends. A cylindrical lens holder 13 projects into the larger-diameter end of the housing and has an outer diameter substantially that of the inner-diameter of the housing. A focusing lens 14 is secured across the inner end of an axially aligned passage in the lens holder. Appropriate means, such as means 15, is provided to secure the device, so that a laser beam may be centered along the axis of the lens holder coaxial with the lens holder and the housing. A two-axis angular orientation device with good rigidity and fine resolution is required at 15.

A radiation detector 17 such as a thermopile or photoelectric element is secured between the end of the housing containing the smaller-diameter passage 12 and an element 18 containing a mirrored inner wall surface 21 coaxially aligned with the passages within the housing and lens holder. The mirrored suface has the shape of a conical section over the greater portion of its length with its base adjacent the detector element. The outer end of the mirrored surface curves toward the axis to a smaller-diameter hole 22. The outer end of the element 18 is on a slight angle to the optical axis so that, if a specular reference mirror is placed along line 27 and is used to reflect radiaton back, the reflected light does not fall on the hole in the radiation detector.

The housing includes a passage 24 therein throhgh which electrical wires 25 pass to connect electrically with the radiation detector.

A radiation shield 26 is placed in back of the axially aligned hole in the radiation detector to minimize the incidence of stray radiation on the back side 29 of the radiation detector. The passage in the radiation shield is only sufficient to pass the main focused beam to a hole 23 in the radiation detector. The hole in the radiation detector is of a particular size. It must be large enough for all or most all of the focused radiation beam to pass to the surface to be checked but small compared to the diameter of the radiation detector. The absolute minimum size for the hole in the detector is given by the diffraction equation for the diameter of an AIRY disc which is:

$d = 2.44 \lambda \, L/D$ where
$d$ = minimum diameter of hole
$\lambda$ = wavelength of the radiation
$L$ = focal length of the lens
$D$ = scan beam diameter For a $CO_2$ laser with a wavelength of about $10^{-5}$ meters and a lens with a 6 centimeter focal length, the minimum hole size will be about 0.01 inch. The ratio of a thermopile detector area to hole area is about 900:1 which will allow very little reflected energy to be lost through the hole in the detector.

The light emergence aperture 22 in the mirrored wall element need be only large enough for the divergent radiation to pass to the object being checked. Also, the radiation is focused by the focusing lens such that the focal point is at or just below the aperture 23 in the radiation detector. Therefore the divergent angle of the radiation at the aperture end 22 of the mirrored surface will be at a minimum for passage of the beam. Yet the minimum diameter of the aperture 22 is greater than that of the aperture 23 in the radiation detector so that the incident radiation on the surface will be greater in diameter than that at the focal point.

One or more screws 16 normal with the lens holder 13 pass through the housing and are provided to adjust the lens holder so that the focusing lens is at a set position along the length of the housing.

The described device may be used for destructive testing. In this case a passage 29 is made in the mirrored wall element so that air, nitrogen, or any other suitable fluid may be forced into the mirrored cavity to prevent material deposits onto the mirrored surface.

Once the device has been assembled, it is properly adjusted by approximtely centering the beam along the axis and adjusting the position of the focusing lens within the housing so that the focal point of the radiation is approximately at the aperture in the radiaton detector. The lens holder is held in place by the screw 16. The two-axis angular orientation device (not shown) is then adjusted to maximize the passage of radiation through hole 23. After proper adjustment of the focusng lens, the device is calibrated.

During calibration, any small amount of detector output due to extraneous radiation on the front of the radiation detector is nulled out by the monitoring circuit. This is, with the radiation passing through apertures 26, 23 and 22 and not reflected back, the monitoring circuit is set at zero. Once the monitoring circuit has been set at zero, a specular reference mirror is placed against the end surface of the mirror surface element in the position represented by the dotted line 27. Since the surface is at an angle with respect to the optical axis of the device, specular reflection does not fall on the aperture on the radiation detector. It is not necessary that a specular reference mirror be used for calibration. However, whatever reflecting calibration surface is used, the monitoring circuit is set at unity or full scale. The device is now ready for measuring the reflectivity of any desired surface with respect to the reference surface.

In use, the surface of an object to be measured is placed against the output end of the reflectometer. The probing beam from the laser is focused through the aperture in the radiation detector and out through the output end of the mirrored wall element. The radiation strikes the surface nearly perpendicularly but at a slight angle due to the slope of the end of the device. The radiation not absorbed by the surface is not reflected straight back but onto the mirrored wall and thence reflected to the detector.

Through normal operation, the radiation incident on the radiation detector will accordingly be represented by the monitoring equipment. In order to obtain a profile of the reflectivity of the surface or to locate the greatest or least reflective portion of the surface, the object may be moved across the end of the reflectometer and the outputs observed or recorded.

With the advent of fiber optics, a fiber bundle can be secured to the input of the reflectometer and the radiation directed from the laser into the fiber bundle and from the fiber bundle into the reflectometer device. By such an arrangement, a small portion of a large stationary object could be checked if desired.

Heat of the detector element is carried off by the body of the housing by conduction. Coolant means may be provided to cool the body of the device, thereby additionally cooling the radiation detector, if desired.

By proper vertical mounting of the reflectometer, measurement of the reflectivities of molten material 31 may be made as shown in FIG. 2. Water-cooling means 32 must be provided for the reflectometer head as well as the injection of a gas into the mirror element through aperture 28 to prevent mirror contamination and provide additional cooling. With this technique, the reflectivity vs temperature profiles can be carried into the molten region, if desired. A temperature monitor 33 may be used to measure the temperature of the molten material.

Obviously many modifications and variations of the present invention are possible in light of the above teachings. It is therefore to be understood that within the scope of the appended claims the invention may be practiced otherwise than as specifically described.

What is claimed and desired to be secured by letters patent of the United States is:

1. A reflectometer for measuring the reflectivity of a test surface which comprises:
   a housing,
   said housing including a large passage in one end and a smaller passage in the opposite end with said passages axially aligned along the length of said housing;
   a lens holder extending into said large passage in said housing with a passage therethrough in coaxial alignment with the large passage in said housing;
   a focusing lens secured on the inner end of said lens holder for focusing light on an optical axis in alignment with the axis of said housing;
   a mirrored wall element including a mirrored conical inner wall secured in axial aignment with said housing coaxial with said optical axis,
   said mirrored wall element including an outlet end with an aperture therein centered on said axis with said outlet end having a curved surface at a slight angle with respect to the optical axis;
   a radiation detector secured betrween said smaller-passage end of said housing and said mirrored wall element,
   said radiation detector including a passage therethrough on the optical axis, and
   means for positioning said lens holder in said housing, whereby radiation focused by said lens will be centered on said aperture in said mirrored wall element and focused to a point at said passage in said radiation detector.

2. A reflectometer as claimed in claim 1 wherein:
said mirrored wall is conical substantially over its length with its base adjacent said radiation detector, and its outlet end curving smoothly to intercept the test surface at an angle of nearly zero degrees.

3. A reflectometer as claimed in claim 2 wherein:
said outlet end of said mirrored wall element is at an angle relative to the axis of the system.

4. A reflectometer as claimed in claim 1, wherein:
said passage through said radiation detector has a minimum diameter
$d = 2.44 \lambda D/L$ where
$d$ = minimum diameter of hole
$\lambda$ = wavelength of the radiation
$L$ = focal length of the lens
$D$ = scan beam diameter.

5. A reflector as claimed in claim 1 which includes:
a radiation shield between said lens and said radiation detector which prevents stray radiation from impinging on said radiation detector.

6. A reflectometer as claimed in claim 3 wherein:
said passage through said radiation detector has a minimum diameter of
$d = 2.44 \lambda D/L$ where
$d$ = minimum diameter of hole
$\lambda$ = wavelength of the radiation
$L$ = focal length of the lens
$D$ = scan beam diameter 7. A reflector as claimed in claim 6 which includes:
a radiation shield between said lens and said radiation detector which prevents stray radiation from impinging on said radiation detector.

* * * * *